United States Patent [19]
Leder et al.

[11] Patent Number: 5,925,803
[45] Date of Patent: Jul. 20, 1999

[54] TESTING METHOD USING TRANSGENIC MICE EXPRESSING AN ONCOGENE

[75] Inventors: Philip Leder, Chestnut Hill, Mass.; Timothy A. Stewart, San Francisco, Calif.

[73] Assignee: President and Fellows of Havard College, Cambridge, Mass.

[21] Appl. No.: 07/750,518

[22] Filed: Sep. 19, 1991

Related U.S. Application Data

[60] Continuation of application No. 07/171,806, Mar. 22, 1988, Pat. No. 5,087,571, which is a division of application No. 06/623,774, Jun. 22, 1984, Pat. No. 4,736,866.

[51] Int. Cl.$^6$ .......................... G01N 33/00; A01K 67/00; A01K 69/00; A01K 67/027
[52] U.S. Cl. .................................. 800/3; 800/10; 800/18; 424/9.2
[58] Field of Search .................................. 800/2, DIG. 1, 800/3, 10, 18; 424/2, 9, 9.2; 435/172.3, 240.2, 317.1; 935/32, 70

[56] References Cited

U.S. PATENT DOCUMENTS

| | | | |
|---|---|---|---|
| 4,535,058 | 8/1985 | Weinberg et al. | 435/6 |
| 4,579,821 | 4/1986 | Palmiter et al. | 435/172.3 |
| 4,873,191 | 10/1989 | Wagner et al. | 435/172.3 |

OTHER PUBLICATIONS

Blair et al., Activation of the Transforming Potential of a Normal Cell Sequence: A Molecular Model for Oncogenesis, Science 212:941–943, 1981.
Brinster et al., Expression of a Microinjected Immunoglobulin Gene in the Spleen of Transgenic Mice, Nature 306:332–336, 1983.
Constantini and Lacy, Introduction of a Rabbit β–globin Gene into the Mouse Germ Line, Nature 294:92, 1981.
Der et al., Transforming Genes of Human Bladder and Lung Carcinoma Cell Lines are Homologous to the ras Genes and Harvey and Kirsten Sarcoma Viruses, Proc. Natl. Acad. Sci. USA 79:3637–3640, 1982.
Ellis et al., The p21 src Genes of Harvey and Kirsten Sarcoma Viruses Originate from Divergent Members of a Family of Normal Vertebrate Genes, Nature 292:506–511, 1981.
Goldfarb et al., Isolation and Preliminary Characterization of a Human Transforming Gene from T24 Bladder Carcinoma Cells, Nature 296:404–409, 1981.
Gorman et al., The Rous Sarcoma Virus Long Terminal Repeat is a Strong Promoter when Introduced into a Variety of Eurkaryotic Cells by DNA–mediated Transfection, Proc. Natl. Acad. Sci. USA 79:6777–6781, 1982.
Huang et al., Glucocorticoid Regulation of the Ha–MuSV p21 Gene Conferred by Sequences from Mouse Mammary Tumor Virus, Cell 27:245–255, 1981.
Lacy et al., A Foreign β–Globin Gene in Transgenic Mice: Integration at Abnormal Chromosomal Positions and Expression in Inappropriate Tissues, Cell 34:343–358, 1983.
McKnight et al., Expression of the Chicken Transferrin Gene in Transgenic Mice, Cell 34:335–341, 1983.
Palmiter, Differential Regulation of Metallothionein–Thymidine Kinase Fusion Genes in Transgenic Mice and Their Offspring, Cell 29:701–710, 1982.
Palmiter et al., Dramatic Growth of Mice that Develop from Eggs Microinjected with Metallothionein–growth Hormone Fusion Genes, Nature 300:611–615, 1982.
Palmiter et al., Metallothionein–Human GH Fusion Genes Stimulate Growth of Mice, Science 222:809–814, 1983.
Schwab et al., Hypersenstivity for Carcinogenesis Resulting from Species . . . Animals Suitable for Monitoring Carcinogens, EPA–600/9–82–013 Sym: Carcinogen. Polynucl. Anomet. Hydrocarbone Mar. Environ, 212–32 (1982).
Shih and Weinberg, Isolation of a Transforming Sequence from a Human Bladder Carcinoma Cell Line, Cell 29:161–169, 1982.
Stewart et al., Human β–Globin Gene Sequences Injected into Mouse Eggs, Retained in Adults, and Transmitted to Progeny, Science 217:1046–1048, 1982.
Ucker et al., Mammary Tumor Virus DNA Contains Sequences Required for its Hormone–Regulated Transcription, Cell 27:257–266, 1981.
Van Brunt, Molecular Farming: Transgenic Animals as Bioreactors, Biotechnology 6:1149–1154, 1988.
Wagner et al., The Human β–Globin and a Functional Viral Thymidine Kinase Gene in Developing Mice, Proc. Natl. Acad. Sci. USA 78:5016–5020, 1981.
Wilmut et al., A Revolution in Animal Breeding, New Scientist, Jul. 7, 1988, pp. 56–59.
Ward et al., Toxicol. Appl. Pharmacol. 51:389–397 (1979).
Schach et al., Fundamental & Appl. Toxicol. 3:631–639 (1983).

*Primary Examiner*—Deborah Crouch
*Attorney, Agent, or Firm*—Clark & Elbing, LLP

[57] ABSTRACT

A transgenic non-human eukaryotic animal whose germ cells and somatic cells contain an activated oncogene sequence introduced into the animal, or an ancestor of the animal, at an embryonic stage.

3 Claims, 2 Drawing Sheets

TESTING METHOD USING TRANSGENIC MICE EXPRESSING AN ONCOGENE

This is a continuation application of U.S. application Ser. No. 07/171,806, filed Mar. 22, 1988, issued as U.S. Pat. No. 5,087,571, which is in turn a divisional application of U.S. application Ser. No. 06/623,774, filed Jun. 22, 1984, issued as U.S. Pat. No. 4,736,866.

BACKGROUND OF THE INVENTION

This invention relates to transgenic animals.

Transgenic animals carry a gene which has been introduced into the germline of the animal, or an ancestor of the animal, at an early (usually one-cell) developmental stage. Wagner et al. (1981) P.N.A.S. U.S.A. 78, 5016; and Stewart et al. (1982) Science 217, 1046 describe transgenic mice containing human globin genes. Constantini et al. (1981) Nature 294, 92; and Lacy et al. (1983) Cell 34, 343 describe transgenic mice containing rabbit globin genes. McKnight et al. (1983) Cell 34, 335 describes transgenic mice containing the chicken transferrin gene. Brinster et al. (1983) Nature 306, 332 describes transgenic mice containing a functionally rearranged immunoglobulin gene. Palmiter et al. (1982) Nature 300, 611 describes transgenic mice containing the rat growth hormone gene fused to a heavy metal-inducible metalothionein promoter sequence. Palmiter et al. (1982) Cell 29, 701 describes transgenic mice containing a thymidine kinase gene fused to a metalothionein promoter sequence. Palmiter et al. (1983) Science 222, 809 describes transgenic mice containing the human growth hormone gene fused to a metalothionein promoter sequence.

SUMMARY OF THE INVENTION

In general, the invention features a transgenic non-human eukaryotic animal (preferably a rodent such as a mouse) whose germ cells and somatic cells contain an activated oncogene sequence introduced into the animal, or an ancestor of the animal, at an embryonic stage (preferably the one-cell, or fertilized oocyte, stage, and generally not later than about the 8-cell stage). An activated oncogene sequence, as the term is used herein, means an oncogene which, when incorporated into the genome of the animal, increases the probability of the development of neoplasms (particularly malignant tumors) in the animal. There are several means by which an oncogene can be introduced into an animal embryo so as to be chromosomally incorporated in an activated state. One method is to transfect the embryo with the gene as it occurs naturally, and select transgenic animals in which the gene has integrated into the chromosome at a locus which results in activation. Other activation methods involve modifying the oncogene or its control sequences prior to introduction into the embryo. One such method is to transfect the embryo using a vector containing an already translocated oncogene. Other methods are to use an oncogene whose transcription is under the control of a synthetic or viral activating promoter, or to use an oncogene activated by one or more base pair substitutions, deletions, or additions.

In a preferred embodiment, the chromosome of the transgenic animal includes an endogenous coding sequence (most preferably the c-myc gene, hereinafter the myc gene), which is substantially the same as the oncogene sequence, and transcription of the oncogene sequence is under the control of a promoter sequence different from the promoter sequence controlling transcription of the endogenous coding sequence. The oncogene sequence can also be under the control of a synthetic promoter sequence. Preferably, the promoter sequence controlling transcription of the oncogene sequence is inducible.

Introduction of the oncogene sequence at the fertilized oocyte stage ensures that the oncogene sequence will be present in all of the germ cells and somatic cells of the transgenic animal. The presence of the onocogene sequence in the germ cells of the transgenic "founder" animal in turn means that all of the founder animal's descendants will carry the activated oncogene sequence in all of their germ cells and somatic cells. Introduction of the oncogene sequence at a later embryonic stage might result in the oncogene's absence from some somatic cells of the founder animal, but the descendants of such an animal that inherit the gene will carry the activated oncogene in all of their germ cells and somatic cells.

Any oncogene or effective sequence thereof can be used to produce the transgenic mice of the invention. Table 1, below, lists some known viral and cellular oncogenes, many of which are homologous to DNA sequences endogenous to mice and/or humans, as indicated. The term "oncogene" encompasses both the viral sequences and the homologous endogenous sequences.

TABLE 1

| Abbreviation | Virus |
| --- | --- |
| src | Rous Sarcoma Virus (Chicken) |
| yes | Y73 Sarcoma Virus (Chicken) |
| fps | Fijirand (St Feline) Sarcoma Virus (Chicken, Cat) |
| abl | Abelson Murine Leukemia Virus (Mouse) |
| rcs | Rocharere Sarcoma Virus (Chicken) |
| frp | Garmen-Rasheed Feline Sarcoma Virus (Cat) |
| ertB | Avian Eryphatlastosis Virus (Chicken) |
| fms | McDonough Feline Sarcoma Virus (Cat) |
| mcs | Moloney Murine Sarcoma Virus (Mouse) |
| raf | 3611 Murine Sarcoma$^+$ Virus (Mouse) |
| Ha-ras-1 | Harvey Murine Sarcoma Virus (Rat) (Balb/c mouse; 2 loci) |
| Ki-ras 2 | Kirsten Murine Sarcoma Virus (Pat) |
| Kr-ras 1 | Kirsten Murine Sarcoma Virus (Pat) |
| myc | Avian MC29 Myelcoyromatosis Virus (Chicken) |
| myt | Avian Myelo Elastomas (Chicken) |
| fos | FBS Ostecsarcoma Virus (Mouse) |
| sft | Avian SET/TLD Virus (Chicken) |
| rel | Reticuloendotheliosis Virus (Turkey) |
| sis | Simian Sarcoma Virus (Wocll7 Monkey) |
| N-myc | Neuroblastomas (Human) |
| N-ras | Neuroblastoma, Leukemia Sarcoma Virus (Human) |

TABLE 1-continued

| Abbreviation | Virus |
| --- | --- |
| Blym | Barsal Lymphomas (Chicken) |
| man | Marrary Carcinoma (Human) |
| neu | Neura, Glioblastoma (Rat) |
| ertA1 | Chicken A37 (Chicken) |
| rs-ras | Rasheed Sarcoma Virus (Rat) |
| mnt-myc | Carcinoma Virus NHE (Chicken) |
| myc | Myelocoytomatosis OKCl (Chicken) |
| myt-ets | Avian myeloblastosis emphroblastosis Virus EB6 (Chicken) |
| raf-1 | 3611-MET(Mouse) |
| raf-1 | 3611-Met (Mouse) |
| Ha-mas-1 | H4-MEV (Fat) |
| ertB | Emphroblastosis virus (Chicken) |

The animals of the invention can be used to test a material suspected of being a carcinogen, by exposing the animal to the material and determining neoplastic growth as an indicator of carcinogenicity. This test can be extremely sensitive because of the propensity of the transgenic animals to develop tumors. This sensitivity will permit suspect materials to be tested in much smaller amounts than the amounts used in current animal carcinogenicity studies, and thus will minimize one source of criticism of current methods, that their validity is questionable because the amounts of the tested material used is greatly in excess of amounts to which humans are likley to be exposed. Furthermore, the animals will be expected to develop tumors much sooner because they already contain an activated oncogene. The animals are also preferable, as a test system, to bacteria (used, e.g., in the Ames test) because they, like humans, are vertebrates, and because carcinogenicity, rather than mutagenicity, is measured.

The animals of the invention can also be used as tester animals for materials, e.g. antioxidants such as beta-carotine or Vitamin E, thought to confer protection against the development of neoplasms. An animal is treated with the material, and a reduced incidence of neoplasm development, compared to untreated animals, is detected as an indication of protection. The method can further include exposing treated and untreated animals to a carcinogen prior to, after, or simultaneously with treatment with the protective material.

The animals of the invention can also be used as a source of cells for cell culture. Cells from the animals may advantageously exhibit desirable properties of both normal and transformed cultured cells: i.e., they will be normal or nearly normal morphologically and physiologically, but can, like cells such as NIH 3T3 cells, be cultured for long, and perhaps indefinite, periods of time. Further, where the promoter sequence controlling transcription of the oncogene sequence is inducible, cell growth rate and other culture characteristics can be controlled by adding or eliminating the inducing factor.

Other features and advantages of the invention will be apparent from the description of the preferred embodiments, and from the claims.

DESCRIPTION OF THE PREFERRED EMBODIMENTS

The drawings will first briefly be described.

Drawings

MMTV-myc Fused Genes

Figure 1:
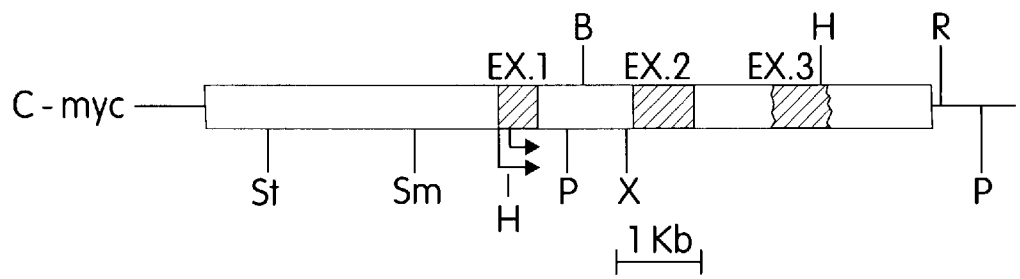
FIG. 1 is a diagrammatic representation of a region of a plasmid bearing the mouse myc gene and flanking regions.

Gene fusions were made using the mouse myc gene and the MMTV LTR. The myc gene is known to be an activatable oncogene. (For example, Leder et al. (1983) Science 222, 765 explains how chromosomal translocations that characterize Burkitt's Lymphoma and mouse plasmacytonas result in a juxtaposition of the myc gene and one of the immunoglobulin constant regions; amplification of the myc gene has also been observed in transformed cell lines.) FIG. 1 illustrates the subclone of the mouse myc gene which provided the myc regions.

Figure 2:
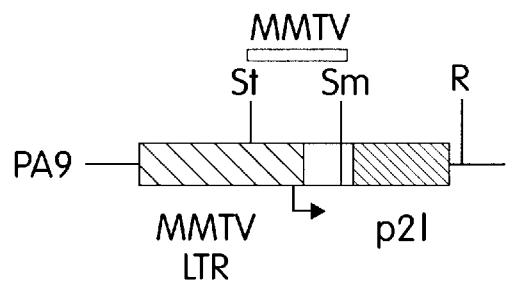
FIG. 2 is a diagrammatic representation of a region of a plasmid, pA9, bearing the mouse mammary tumor virus long terminal repeat (MMTV LTR) sequences.
Figure 3:
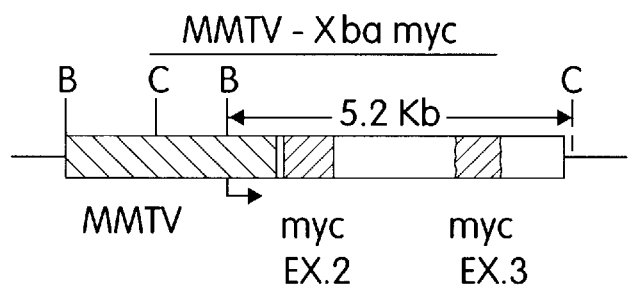
FIGS. 3–6 and 8 are diagrammatic representations of activated oncogene fusions.

The required MMTV functions were provided by the pA9 plasmid (FIG. 2) that demonstrated hormone inducibility of the p21 protein: this plasmid is described in Huang et al. (1981) Cell 27, 245. The MMTV functions on pA9 include the region required for glucocorticoid control, the MMTV promoter, and the cap site.

The above plasmids were used to construct the four fusion gene contructions illustrated in FIGS. 3–6. The constructions were made by deleting from pA9 the Sma-EcoRI region that included the P21 protein coding sequences, and replacing it with the four myc regions shown in the Figures. Procedures were the conventional techniques described in Maniatis et al. (1982) Molecular Cloning: A Laboratory Manual (Cold Spring Harbor Laboratory). The restriction sites shown in FIG. 1 are StuI (St), SmaI (Sm), EcoRI (R), HindIII (H), PvuI (P), BamHl (B), XbaI (X), and ClaI (C). The solid arrows below the constructions represent the promoter in the MMTV LTR and in the myc gene. The size (in Kb) of the major fragment, produced by digestion with BamHI and ClaI, that will hybridize to the myc probe, is shown for each construction.

MMTV-H3 myc (FIG. 5) was constructed in two steps: Firstly, the 4.7 Kb Hind III myc fragment which contains most of the myc sequences was made blunt with Klenow polymerase and ligated to the pA9 SmaI-EcoRI vector that had been similarly treated. This construction is missing the normal 3' end of the myc gene. In order to introduce the 3' end of the myc gene, the PvuI-PvuI fragment extending from the middle of the first myc intron to the pBR322 PvuI site in the truncated MMTV-H3 myc was replaced by the related PvuI-PvuI fragment from the mouse myc subclone.

The MMTV-Xba myc construction (FIG. 3) was produced by first digesting the MMTV-Sma myc plasmid with SmaI and XbaI. The XbaI end was then made blunt with Klenow polymerase and the linear molecule recircularized with T4 DNA ligase. The MMTV-Stu myc (FIG. 6) and the MMTV-Sma myc (FIG. 4) constructions were formed by replacing the P21 protein coding sequences with, respectively, the StuI-EcoRI or SmaI-EcoRI myc fragments (the EcoRI site is within the pBR322 sequences of the myc subclone). As shown in FIG. 1, there is only one StuI site within the myc gene. As there is more than one SmaI site within the myc gene (FIG. 4), a partial SmaI digestion was carried out to generate a number of MMTV-Sma myc plasmids; the plasmid illustrated in FIG. 4 was selected as not showing rearrangements and also including a sufficiently long region 5' of the myc promoter (approximately 1 Kb) to include myc proximal controlling regions.

Figure 4:
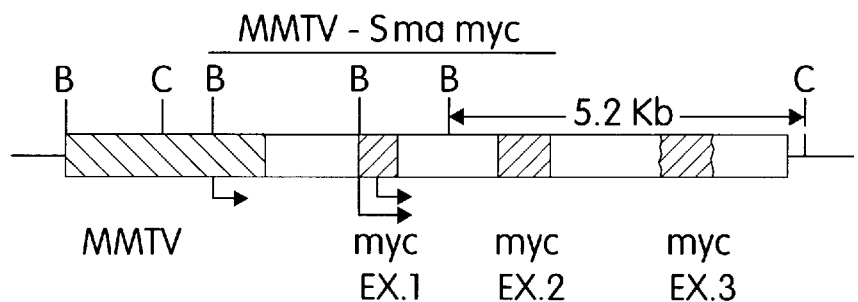
Figure 5:
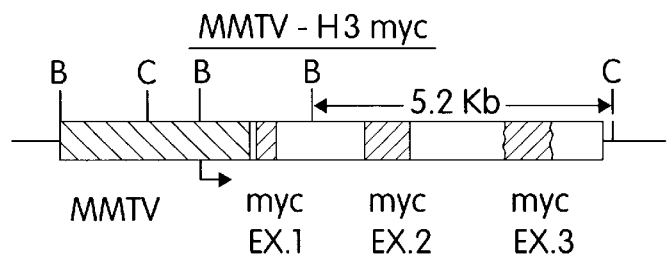
Figure 6:
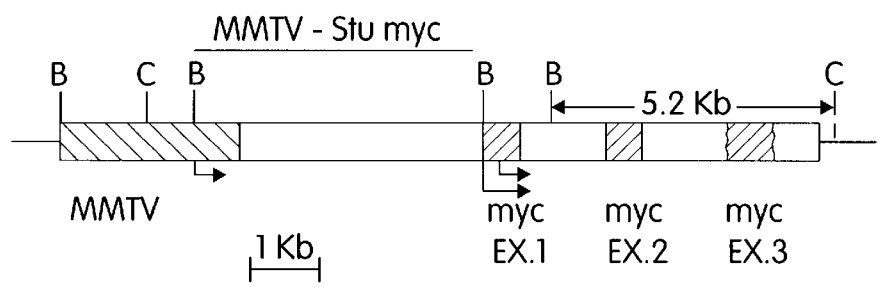

The constructions of FIGS. 4 and 6 contain the two promoters naturally preceding the unactivated myc gene. The contruction of FIG. 5 has lost both myc promoters but retains the cap site of the shorter transcript. The construction of FIG. 3 does not include the first myc exon but does include the entire protein coding sequence. The 3' end of the myc sequence in all of the illustrated constructions is located at the HindIII site approximately 1 kb 3' to the myc polyA addition site.

These constructions were all checked by multiple restriction enzyme digestions and were free of detectable rearrangements.

Production of Transgenic Mice Containing MMTV-myc Fusions

The above MMTV-myc plasmids were digested with SalI and EcoRI (each of which cleaves once within the pBR322 sequence) and separately injected into the male pronuclei of fertilized one-cell mouse eggs; this resulted in about 500 copies of linearized plasmid per pronucleus. The injected eggs were then transferred to pseudo-pregnant foster females as described in Wagner et al. (1981) P.N.A.S. U.S.A. 78, 5016. The eggs were derived from a CD-1 X C57B1/6J mating. Mice were obtained from the Charles River Laboratories ($CD^R$-1-Ha/Icr (CD-1), an albino outbred mouse) and Jackson Laboratories (C57B1/6J), and were housed in an environmentally controlled facility maintained on a 10 hour dark: 14 hour light cycle. The eggs in the foster females were allowed to develop to term.

Analysis of Transgenic Mice

At four weeks of age, each pup born was analyzed using DNA taken from the tail in a Southern hybridization, using a $^{32}P$ DNA probe (labeled by nick-translation). In each case, DNA from the tail was digested with BamHI and ClaI and probed with the $^{32}P$-labeled BamHI/HindIII probe from the normal myc gene (FIG. 1).

The DNA for analysis was extracted from 0.1–1.5 cm sections of tail, by the method described in Davis et al. (1980) in Methods in Enzymology, Grossman et al., eds., 65, 404, except that one chloroform extraction was performed prior to ethanol precipitation. The resulting nucleic acid pellet was washed once in 80% ethanol, dried, and resuspended in 300 $\mu$l of 1.0 mM Tris, pH 7.4, 0.1 mM EDTA.

Ten $\mu$l of the tail DNA preparation (approximately 10 $\mu$g DNA) were digested to completion, electrophoresed through 0.8% agarose gels, and transferred to nitrocellulose, as described in Southern (1975) J. Mol. Biol. 98, 503. Filters were hybridized overnight to probes in the presence of 10% dextran sulfate and washed twice in 2 X SSC, 0.1% SDS at room temperature and four times in 0.1 X SSC. 0.1% SDS at 64° C.

The Southern hybridizations indicated that ten founder mice had retained an injected MMTV-myc fusion. Two founder animals had integrated the myc gene at two different loci, yielding two genetically distinct lines of transgenic mice. Another mouse yielded two polymorphic forms of the integrated myc gene and thus yielded two genetically distinct offspring, each of which carried a different polymorphic form of the gene. Thus, the 10 founder animals yielded 13 lines of transgenic offspring.

The founder animals were mated to uninjected animals and DNA of the resulting thirteen lines of transgenic offspring analyzed; this analysis indicated that in every case the injected genes were transmitted through the germline. Eleven of the thirteen lines also expressed the newly acquired MMTV-myc genes in at least one somatic tissue; the tissue in which expression was most prevelant was salivary gland.

Figure 7:
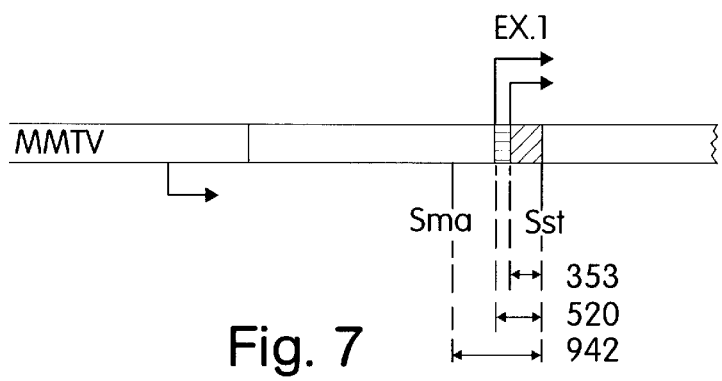
FIG. 7 is a diagrammatic representation of a probe useful for detecting activated myc fusions.

Transcription of the newly acquired genes in tissues was determined by extracting RNA from the tissues and assaying the RNA in an S1 nuclease protection procedure, as follows. The excised tissue was rinsed in 5.0 ml cold Hank's buffered saline and total RNA was isolated by the method of Chrigwin et al. (1979) Biochemistry 18, 5294, using the CsCl gradient modification. RNA pellets were washed twice by reprecipitation in ethanol and quantitated by absorbance at 260 nm. An appropriate single stranded, uniformly labeled DNA probe was prepared as described by Ley et al. (1982) PNAS USA 79, 4775. To test for transcription of the MMTV-Stu myc fusion of FIG. 6, for example, the probe illustrated in FIG. 7 was used. This probe extends from a SmaI site 5' to the first myc exon to an SstI site at the 3' end of the first myc exon. Transcription from the endogenous myc promoters will produce RNA that will protect fragments of the probe 353 and 520 base pairs long; transcription from the MMTV promoter will completely protect the probe and be revealed as a band 942 base pairs long, in the following hybridization procedure.

Labelled, single-stranded probe fragments were isolated on 8M urea 5% acrylamide gels, electroeluted, and hybridized to total RNA in a modification of the procedure of Berk et al. (1977) Cell 12, 721. The hybridization mixture contained 50,000 cpm to 100,000 cpm of probe (SA=$10^8$ cpm/$\mu$g), 10 $\mu$g total cellular RNA, 75% formamide, 500 mM NaCl, 20 mM Tris pH 7.5, 1 mM EDTA, as described in Battey et al. (1983) Cell 34, 779. Hybridization temperatures were varied according to the GC content in the region of the probe expected to hybridize to mRNA. The hybridizations were terminated by the addition of 1500 units of S1 nuclease (Boehringer Mannheim). S1 nuclease digestions were carried out at 37° C. for 1 hour. The samples were then ethanol-precipitated and electrophoresed on thin 8M urea 5% acrylamide gels.

Northern hybridization analysis was also carried out, as follows. Total RNA was electrophoresed through 1% formaldehyde 0.8% agarose gels, blotted to nitrocellulose filters (Lehrach et al. (1979) Biochemistry 16, 4743), and hybridized to nick-translated probes as described in Taub et al. (1982) PNAS USA 79, 7837. The tissues analyzed were thymus, pancreas, spleen, kidney, testes, liver, heart, lung, skeletal muscle, brain, salivary gland, and preputial gland.

Both lines of mice which had integrated and were transmitting to the next generation the MMTV-Stu myc fusion (FIG. 6) exhibited transcription of the fusion in salivary gland, but in no other tissue.

One of two lines of mice found to carry the MMTV-Sma myc fusion (FIG. 4) expressed the gene fusion in all tissues examined, with the level of expression being particularly high in salivary gland. The other line expressed the gene fusion only in salivary gland, spleen, testes, lung, brain, and preputial gland.

Four lines of mice carried the MMTV-H3 myc fusion (FIG. 5). In one, the fusion was transcribed in testes, lung, salivary gland, and brain; in a second, the fusion was transcribed only in salivary gland; in a third, the fusion was transcribed in none of the somatic tissues tested; and in a fourth, the fusion was transcribed in salivary gland and intestinal tissue.

In two mouses lines found to carry the MMTV-Xba myc fusion, the fusion was transcribed in testes and salivary gland.

RSV-myc Fused Genes

Figure 8:
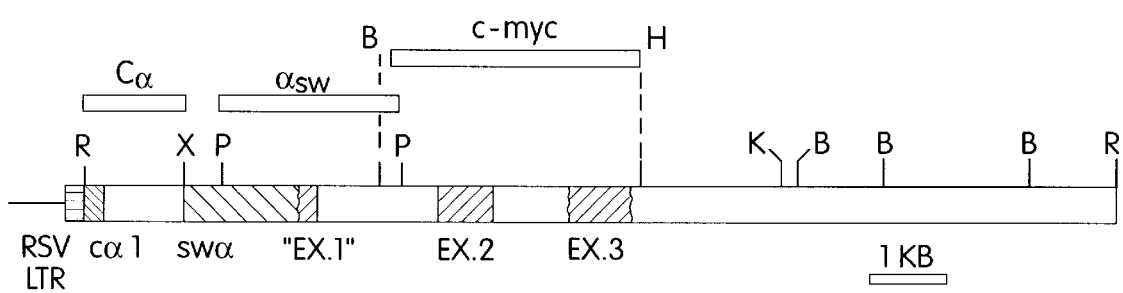

Referring to FIG. 8, the plasmid designated RSV-S107 was generated by inserting the EcoRI fragment of the S107 plasmacytoma myc gene, (Kirsch et al. (1981) Nature 293, 585) into a derivative of the Rous Sarcoma Virus (RSV) enhancer-containing plasmid (pRSVcat) described in Gorman et al. (1982) PNAS USA 79, 6777, at the EcoRI site 3' to the RSV enhancer sequence, using standard recombinant DNA techniques. All chloramphenicol acetyl transferase and SV40 sequences are replaced in this vector by the myc gene: the RSV promoter sequence is deleted when the EcoRl fragments are replaced, leaving the RSV enhancer otherwise intact. The original translocation of the myc gene in the S107 plasmacytoma deleted the two normal myc promoters as well as a major portion of the untranslated first myc exon, and juxtaposed, 5' to 5', the truncated myc gene next to the a immunoglobulin heavy chain switch sequence.

The illustrated (FIG. 8) regions of plasmid RSV-S107 are: crosshatched, RSV sequences; fine-hatched, alpha 1 coding sequences: left-hatched, immunoglobulin alpha switch sequences; right-hatched, myc exons. The thin lines flanking the RSV-S107 myc exon represent pBR322 sequences. The marked restriction enzyme sites are: R, EcoRI: X, Xbal; P, Pst 1: K, Kpn 1: H, HindIII; B, BamHI. The sequences used for three probes used in assays described herein (C-$^\alpha$, $^\alpha$-sw and c-myc) are marked.

Production of Transgenic Mice

Approximately 500 copies of the RSV-S107 myc plasmid (linearized at the unique Kpn-1 site 3' to the myc gene) were injected into the male pronucleus of eggs derived from a C57BL/6J×CD-1 mating. Mice were obtained from Charles River Laboratories (CD-1, an albino outbred mouse) and from Jackson Laboratories (C57BL/6J). These injected eggs were transferred into pseudopregnant foster females, allowed to develop to term, and at four weeks of age the animals born were tested for retention of the injected sequences by Southern blot analysis of DNA extracted from the tail, as described above. Of 28 mice analyzed, two males were found to have retained the new genes and both subsequently transmitted these sequences through the germline in a ratio consistent with Mendelian inheritance of single locus.

First generation transgenic offspring of each of these founder males were analyzed for expression of the rearranged myc genes by assaying RNA extracted from the major internal tissues and organs in an S1 nuclease protection assay, as described above. The hearts of the offspring of one line showed aberrant myc expression; the other 13 tissues did not.

Backcrossing (to C57B1/6J) and in-breeding matings produced some transgenic mice which did not demonstrate the same restriction site patterns on Southern blot analysis as either their transgenic siblings or their parents. In the first generation progeny derived from a mating between the founder male and C57BL/6J females, 34 F1 animals were analyzed and of these, 19 inherited the newly introduced gene, a result consistent with the founder being a heterozygote at one locus. However, of the 19 transgenic mice analyzed, there were three qualitatively different patterns with respect to the more minor myc hybridizing fragments.

In order to test the possibility that these heterogenous genotypes arose as a consequence of multiple insertions and/or germline mosacism in the founder, two F1 mice (one carrying the 7.8 and 12 Kb BamHI bands, and the other carrying only the 7.8 Kb BamHI band) were mated and the F2 animals analyzed. One male born to the mating of these two appeared to have sufficient copies of the RSV-S107 myc gene to be considered as a candidate for having inherited the two loalleles; this male was backcrossed with a wild-type female. All 23 of 23 backcross offspring analyzed inherited the RSV-S107 myc genes, strongly suggesting that the F2 male mouse had inherited two alleles at one locus. Further, as expected, the high molecular weight fragment (12 Kb) segregated as a single allele.

To determine whether, in addition to the polymorphisms arising at the DNA level, the level of aberrant myc expression was also altered, heart mRNA was analyzed in eight animals derived from the mating of the above double heterozygote to a wild-type female. All eight exhibited elevated myc mRNA, with the amount appearing to vary between animals; the lower levels of expression segregated with the presence of the 12 Kb myc hybridizing band. The level of myc mRNA in the hearts of transgenic mice in a second backcross generation also varied. An F1 female was backcrossed to a C57B1/6J male to produce a litter of seven pups, six of which inherited the RSV-S107 myc genes. All seven of these mice were analyzed for expression. Three of the six transgenic mice had elevated levels of myc mRNA in the hearts whereas in the other three the level of myc mRNA in the hearts was indistinguishable from the one mouse that did not carry the RSV-S107 myc gene. This result suggests that in addition to the one polymorphic RSV-S107 myc locus from which high levels of heart-restricted myc mRNA were transcribed, there may have been another segregating RSV-S107 myc locus that was transcriptionally silent.

Carcinogenicity Testing

The animals of the invention can be used to test a material suspected of being a carcinogen, as follows. If the animals are to be used to test materials thought to be only weakly carcinogenic, the transgenic mice most susceptible of developing tumors are selected, by exposing the mice to a low dosage of a known carcinogen and selecting those which first develop tumors. The selected animals and their descendants are used as test animals by exposing them to the material suspected of being a carcinogen and determining neoplastic growth as an indicator of carcinogenicity. Less sensitive animals are used to test more strongly carcinogenic materials. Animals of the desired sensitivity can be selected by varying the type and concentration of known carcinogen used in the selection process. When extreme sensitivity is desired, the selected test mice can consist of those which spontaneously develop tumors.

Testing for Cancer Protection

The animals of the invention can be used to test materials for the ability to confer protection against the development of neoplasms. An animal is treated with the material, in parallel with an untreated control transgenic animal. A comparatively lower incidence of neoplasm development in the treated animal is detected as an indication of protection.

Tissue Culture

The transgenic animals of the invention can be used as a source of cells for cell culture. Tissues of transgenic mice are analyzed for the presence of the activated oncogene, either by directly analyzing DNA or RNA, or by assaying the tissue for the protein expressed by the gene. Cells of tissues carrying the gene can be cultured, using standard tissue culture techniques, and used. e.g., to study the functioning of cells from normally difficult to culture tissues such as heart tissue.

Deposits

Plasmids bearing the fusion genes shown in FIGS. 3, 4, 5, 6, and 8 have been deposited in the American Type Culture Collection, Rockville, Md. and given, respectively, ATCC Accession Nos. and

OTHER EMBODIMENTS

Other embodiments are within the following claims. For example, any species of transgenic animal can be employed. In some circumstances, for instance, it may be desirable to use a species, e.g., a primate such as the rhesus monkey, which is evolutionarily closer to humans than mice.

We claim:

1. A method of testing a material suspected of being a carcinogen, comprising exposing a transgenic mouse to said material and detecting neoplasms as an indication of carcinogenicity, wherein the germ cells and somatic cells of said mouse contain an activated oncogene sequence introduced into said mouse, or an ancestor of said mouse, at an embryonic stage.

2. A method of testing a material suspected of conferring protection against the development of neoplasms, said method comprising (1) providing a first and a second transgenic mouse, the germ cells and somatic cells of which contain an activated oncogene sequence introduced into said mice, or an ancestor of said mice, at an embryonic stage, (2) treating said first mouse with said material, and (3) detecting, as an indication of said protection, a reduced incidence of development of neoplasms in said first mouse, compared to the incidence in said second mouse, which is not so treated.

3. The method of claim 1, further comprising exposing said first and second mice to a carcinogen prior to, after, or simultaneously with treating said first mouse with said material.

* * * * *

UNITED STATES PATENT AND TRADEMARK OFFICE
CERTIFICATE OF CORRECTION

| | | |
|---|---|---|
| PATENT NO. | : 5,925,803 | Page 1 of 1 |
| APPLICATION NO. | : 07/750518 | |
| DATED | : July 20, 1999 | |
| INVENTOR(S) | : Leder et al. | |

It is certified that error appears in the above-identified patent and that said Letters Patent is hereby corrected as shown below:

Column 10, line 13, replace "1" with --2--.

Signed and Sealed this
Eighth Day of February, 2011

David J. Kappos
*Director of the United States Patent and Trademark Office*

(12) EX PARTE REEXAMINATION CERTIFICATE (8325th)
United States Patent
Leder et al.

(10) Number: US 5,925,803 C1
(45) Certificate Issued: Jun. 14, 2011

(54) TESTING METHOD USING TRANSGENIC MICE EXPRESSING AN ONCOGENE

(76) Inventors: Philip Leder, Chestnut Hill, MA (US); Timothy A. Stewart, San Francisco, CA (US)

Reexamination Request:
No. 90/010,955, Apr. 20, 2010

Reexamination Certificate for:
Patent No.: 5,925,803
Issued: Jul. 20, 1999
Appl. No.: 07/750,518
Filed: Sep. 19, 1991

Certificate of Correction issued Feb. 8, 2011.

Related U.S. Application Data

(63) Continuation of application No. 07/171,806, filed on Mar. 22, 1988, now Pat. No. 5,087,571.

(51) Int. Cl.
*G01N 33/00* (2006.01)

(52) U.S. Cl. ............................ 800/3; 800/10; 800/18; 424/9.2

(58) Field of Classification Search ................. None
See application file for complete search history.

(56) References Cited

U.S. PATENT DOCUMENTS

| 4,360,510 A | 11/1982 | Proctor |
| 4,736,866 A | 4/1988 | Leder et al. |

OTHER PUBLICATIONS

Brinster et al., "Transgenic mice harboring SV40 T–antigen genes develop characteristic brain tumors," *Cell*, 37:367–79, 1984.

Interlocutory Decision in Opposition Proceedings (Articles 102(3) and 106(3) EPC) for European Patent Application No. 85304490.7, Jan. 16, 2003.

Jaenisch and Mintz, "Simian virus 40 DNA sequences in DNA of healthy adult mice derived from preimplantation blastocysts injected with viral DNA," *Pro. Natl. Acad. Sci. USA*, 71:1250–4, 1974.

Leder et al., "Translocations among antibody genes in human cancer," *Science*, 222:765–71, 1983.

Minutes of the Oral Proceedings for European Patent Application No. 85304490.7 and Annex 4 of the Minutes, Nov. 24, 1995.

Office Action for Canadian Patent Application No. 484,723, Feb. 21, 1990.

Office Action for Canadian Patent Application No. 484,723, Jan. 14, 1992.

Reply to Office Action for Canadian Patent Application No. 484,723, Aug. 16, 1990.

Reply to Office Action for Canadian Patent Application No. 484,723, Jul. 14, 1992.

Translation of Notice of Reason for Rejection for Japanese Patent Application No. 60–134452, Aug. 13, 1992.

Ward et al., Toxicol., Appl. Pharmacol., 51:389–397 (1979).

Schach et al., Fund. Appl. Toxicol., 3:631–639 (1983).

Schwab et al., EPA–600/9–82–013, Sym: Carcinogen, Polynucl. Aromat. Hydrocarbons Mar. Environ., 212–32 (1982).

Jaenisch et al., PNAS, USA, 71(4):1250–1254 (1974).

*Primary Examiner*—Brenda Brumback

(57) ABSTRACT

A transgenic non-human eukaryotic animal whose germ cells and somatic cells contain an activated oncogene sequence introduced into the animal, or an ancestor of the animal, at an embryonic stage.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 2 and 3 is confirmed.

* * * * *